| United States Patent [19] | [11] | 4,224,412 |
|---|---|---|
| Dorofeev et al. | [45] | Sep. 23, 1980 |

[54] LIVING VIRUS CULTURE VACCINE AGAINST CANINE DISTEMPER AND METHOD OF PREPARING SAME

[76] Inventors: Viktor M. Dorofeev, Snaiperskaya ulitsa, 3, kv. 48; Evelina G. Birjukova, Novo-Basmannaya ulitsa, 15, kv. 8; Otar G. Andzhaparidze, Sadovo-Sukharevskaya ulitsa, 8/12, kv. 43; Oleg A. Metelkin, Nikitinskaya ulitsa, 21-2, kv. 48; Evgeny P. Danilov, Samarsky bulvar, 15, korpus 3, kv. 21; Vera I. Geller, ulitsa Starogo gaya, 1, korpus 3, kv. 20, all of Moscow, U.S.S.R.

[21] Appl. No.: 35,065

[22] Filed: May 1, 1979

[51] Int. Cl.$^2$ ............................................... C12N 7/08
[52] U.S. Cl. .................................................... 435/237
[58] Field of Search ........................... 195/1.3; 435/237

[56] References Cited

U.S. PATENT DOCUMENTS

| 2,912,361 | 10/1959 | Froelich | 435/237 |
|---|---|---|---|
| 2,965,544 | 12/1960 | Cabasso | 435/237 |
| 3,098,011 | 7/1963 | Rockborn | 435/237 |
| 3,354,038 | 11/1967 | Bass | 195/1.3 |
| 3,836,626 | 9/1974 | Lavender | 195/1.3 |
| 4,004,974 | 1/1977 | Chumakov et al. | 195/1.3 |
| 4,071,618 | 1/1978 | Konobe et al. | 195/1.3 |

*Primary Examiner*—Frederick E. Waddell
*Attorney, Agent, or Firm*—Fleit & Jacobson

[57] ABSTRACT

Said vaccine comprises an attenuated strain EPM 10-76 of the virus of canine distemper, obtained from the wild virus, isolated from a mink with distemper, by multiple passage in cell cultures of various origin: dog kidney cell culture, continuous cell culture of the kidneys of human embryo Rh, and a mixed cell culture consisting of dog kidney cells and Japanese quail embryo cells, adapted to the Japanese quail embryo cell culture and grown on this culture.

The method of preparing said vaccine consists in inoculating the Japanese quail embryo cell culture with said strain and incubating it on said culture.

The advantage of the proposed vaccine is that it is harmless, highly immunogenic and antigenic, as well as it is cheap. The proposed vaccine does not contain extraneous viruses and can be used for both prophylaxis of canine distemper and for eradication of the epizootia. The vaccine in aerosol form can also be used for vaccination.

5 Claims, No Drawings

LIVING VIRUS CULTURE VACCINE AGAINST CANINE DISTEMPER AND METHOD OF PREPARING SAME

FIELD OF THE INVENTION

The present invention relates to veterinary and more particularly to a living virus culture vaccine against canine distemper and the method of preparing same.

Canine distemper is an acute contagious disease of fur-bearing animals and dogs. Young minks, silver and blue fox are especially susceptible to the disease. The high lethality and the absence of effective therapeutic means are the cause of great econimic damage to fur-bearing animal breeding.

BACKGROUND OF THE INVENTION

Known in the prior art are living virus culture vaccines used for prophylaxis of canine distemper. The vaccines contain attenuated strains of distemper viruses adapted to cell cultures of dog or monkey kidneys, or chick embryos.

The "Rockborn" vaccine comprising an attenuated strain of the canine distemper virus, obtained from a wild strain, isolated from the blood of a dog affected with distemper, is prepared on a dog kidney culture cell. To prepare the vaccine, said strain is adapted to the dog kidney cell culture by over 50 passages, and cultivated on said cell culture in a Hanks' solution containing 0.5 percent of lactalbumin hydrolysate and 10 percent of horse serum, or 20 percent of calf serum, or on Earle's medium containing 0.5 percent of lactalbumin hydrolysate and 2 percent of horse or calf serum. The temperature of adaptation is maintained at 30°–37° C., preferably at 35°–37° C. The obtained vaccine is then stabilized and lyophilized (see U.S. Pat. No. 3,098,011).

Known in the prior art is also a vaccine against canine distemper prepared by ten passages of the virus on a cell culture of dog kidneys in the Earle's medium containing 5 percent of lactalbumin hydrolysate and 5 percent of horse serum at a temperature of 38.5° C. (U.S. Pat. No. 3,354,038).

Said vaccines have high immunogenic activity but there are also some disadvantages inherent in them, one of which is low reproducibility of the virus in the dog kidney cell culture.

Another disadvantage of said vaccines is that dog kidney cell culture is used as the substrate for attenuation of the virus and production of vaccines, but dog kidneys can be contaminated with some other viruses, and a special vivarium is required to keep the dogs away from uncontrollable infection. This envolves extra expenditures.

Still another disadvantage of the vaccines is that it is difficult to determine their biological activity, since the virus reproduction is associated with an indistinctly manifest cytopathogenic action that shows by the 20th day following the infection when nonspecific degenerative changes in the cell can develop and interfere with the assessment of the result.

Still another disadvantage inherent in the known vaccines prepared on the dog kidney cell culture is the slow growth of the cells (a monolayer of cells is only formed by the 5th to 7th day) and this prolongs the process of preparing the vaccine.

Viral vaccines intended to control canine distemper animals obtained by cultivating the virus strain on a 9-day chick embryo cell culture or on chorioallantoic membranes of chick embryo can present danger because of the high contamination of chick embryo with some other viruses, and with viruses of the leukemia-sarcomatous group in particular (see U.S. Pat. Nos. 2,912,361 and 2,965,544).

A vaccine prepared on the chick embryo cell culture from the strain known in the USSR as KF-668 has the same disadvantage.

The American vaccine ASL is harmless and devoid of said disadvantage because it is prepared in the cell culture of chick embryos not affected by leukemia, but special farms are required where such leukemia-free poultry can be raised, which, involves additional expenditures. Moreover, the vaccinal strain of the virus does not produce regular cytopathic action in the chick embryo cell culture which complicates the process of the vaccine production.

Known in the prior art is also a viral vaccine against canine distemper prepared by cultivating the virus of canine distemper on the cell culture of kidneys of green monkeys (cf. U.S. Pat. No. 4,004,974). This vaccine is sufficiently immunogenic, areactogenic, highly standard, and harmless. However, monkey hunting becomes now a difficult problem because of the reduction of their populations. The manufacture of this vaccine is based on the utilization of the waste of poliomyelitis vaccine production and is thus closely connected with this process. It is easy to understand that the construction of an independent facility for the manufacture of the distemper vaccine based on the cell culture of monkey kidneys will be very expensive.

The selection of the cell substrate for the manufacture of the viral vaccine thus seems difficult. The imperative prerequisite is the absence of contamination of the cell substrate with extraneous viruses and also production of the vaccine virus in sufficient amounts.

SUMMARY OF THE INVENTION

It is an object of this invention to provide a cheap and harmless vaccine against canine distemper exhibiting high immunogenic and antigenic activity.

Another object of the invention is to provide a vaccine against canine distemper that will be free from other viruses pathogenic to said animals and man, especially the viruses of the leukemia-sarcomatous group.

A further object of the invention is to provide a highly immunogenic strain of the virus of canine distemper that can be cultivated on safe and readily available substrate.

Still another object of the invention is to provide a method for manufacture of the vaccine against canine distemper having the above properties.

Yet another object of the invention is to develop a method for the manufacture of said vaccine based on inexpensive and readily available materials.

According to the invention, there is proposed a living virus culture vaccine against canine distemper comprising the attenuated strain EPM of the virus of canine distemper deposited under the code number of 10-76, obtained from the wild virus isolated from the blood of a mink affected by distemper, by repeated passage on the following cell cultures: (1) dog kidney cell culture, (2) continuous cell culture of kidneys of human embryo Rh, (3) mixed culture consisting of cells of dog kidneys and cells of Japanese quail embryos, adapted to the cell culture of Japanese quail embryos and grown on this culture.

According to the invention, there is also proposed a method for preparing a living virus culture vaccine against canine distemper, comprising cultivation, on the cell culture of Japanese quail embryos in a suitable medium, of the virus of canine distemper, EPM, deposited under the number of 10-76, obtained from the wild virus isolated from the blood of a mink affected with distemper, by repeated passage on the following cell cultures: (1) dog kidney cell culture, (2) continuous cell culture of human embryo kidneys Rh, (3) mixed culture consisting of dog kidney cells and cells of Japanese quail embryos, with subsequent adaptation to the cell culture of embryos of Japanese quail embryos; collection of the obtained virus-containing fluid; lyophilic drying of the virus-containing fluid in the presence of a suitable stabilizer.

Said attenuated strain of the virus, which is used for the manufacture of the vaccine against canine distemper, is given the name of EPM strain of virus of canine distemper. The capital letters EPM stand for embryo, quail (Russian perepiolka), and Moscow, respectively.

Said strain is a novel vaccine strain. It is deposited with the All-Union State Institute for Veterinary Preparations of the Ministry of Agriculture of the USSR, where it has been assigned the number of 10-76.

The EPM strain of virus of canine distemper has been obtained from the wild virus isolated from the blood of a mink affected with distemper, by 20-40-fold passage on a cell culture of dog kidneys at a temperature of $37\pm1°$ C. with subsequent 5-15 passages on the cell culture of the human embryo kidney Rh at a temperature of $32\pm1°$ C. and 2-7 passages on the mixed culture consisting of kidney cells of the dog and Japanese quail embryo cells, at a temperature of $35\pm1°$ C. with subsequent adaptation by 4 to 10 passages on the cell culture of Japanese quail (*Coturnix coturnix japonica*) embryos.

To prepare the vaccine, said strain is cultivated on the cell culture of Japanese quail embryos in a suitable culture mediam, e.g. medium 199, or Earle's medium containing 10 percent of cattle blood serum. The first harvest of the virus-containing fluid is collected after development of the cytopathic action of the virus in 20 to 40 percent of the cells. The collected culture fluid is dried liophilically in the presence of a suitable stabilizer, e.g., in the presence of 4.5-5.5 percent sorbitol and 1.4-1.6 percent of gelatose.

The vaccine strain EPM 10-76 of the virus of carnivores is a highly attenuated strain well propagating in the cell culture of Japanese quail embryos characterized by distinct cytopathic action, which markedly simplifies the process of production of the vaccine. Said strain is stable in storage.

The advantages of the proposed vaccine are as follows:

(a) the vaccine is harmless, it does not produce toxic action, and is manufactured in the cell culture of Japanese quail embryos, which is an inexpensive and readily available material that can reliably be controlled for the absence of extraneous viruses; Japanese quails are naturally insusceptible to the leukemia-sarcomatous group viruses and the cell culture of their embryos is the optimum substrate for the manufacture of the viral vaccine;

(b) the cell culture of Japanese quail ambryos has high proliferative activity which makes it possible to infect the cell suspension without formation of the cell monolayer;

(c) the vaccine has high antigenic activity, it produces effective and persistent immunity in the vaccinated animals, and the vaccination in the epizootic foci of canine distemper rapidly eradicates the infection;

(d) the vaccine can be given parenterally and in aerosol form, which simplifies markedly the prophylactic measures and makes them cheaper;

(e) the vaccine is highly active and the commercial preparation can therefore be filled in vials or ampoules in quantities ranging from 1 to 500 doses, which is very convenient for individual or mass-scale use use of the vaccine.

These and other advantages of the invention will become subsequently clear from the detailed description of the vaccine and of the method of its manufacture and use.

DETAILED DESCRIPTION OF THE INVENTION

The method of preparing the living virus culture vaccine is based on the virus inoculation principle. The principle consists in preparing a large amount of the vaccinal virus that meets all requirements for the attenuated strain, in keeping this virus in the frozen state, and using it to prepare the vaccine.

As has already been stated, the attenuated strain EPM No. 10-76, is used to prepare the vaccine against canine distemper.

Said strain has been obtained from the wild virus of canine distemper isolated from the blood of a mink with distemper. This wild strain is attenuated by multiple passage on various cell cultures in the following sequence:

(1) 20-40 passages on the dog kidney cell culture at a temperature of $37\pm1°$ C.;

(2) 5-15 passages on a continuous cell culture of kidneys of human embryo Rh at a temperature of $32\pm1°$ C.; and (3) 2-7 passages on a mixed culture consisting of a dog kidney cells and cells of Japanese quail embryos at a temperature of $35\pm1°$ C.

The attenuated virus is adapted to the cell culture of Japanese quail embryos by 4 to 10 passages. The obtained strain is cloned in the cell culture of Japanese quail embryos by the limit dilution method. All these operations give the strain of the virus with marked cypopathic activity which makes it possible to control the process of preparing the vaccine, to harvest the virus in optimum terms, to simplify significantly the determination of the infectious activity of the virus, and moreover to determine specificity of the virus in the cell culture and to reveal antibodies in the blood serum of vaccinated animals. The obtained virus strain is characterized by the following:

(1) specificity in the neutralization test on the cell culture of Japanese quail embryos;

(2) harmlessness for laboratory animals, e.g. mice, guinea pigs, rabbits, chick embryos, and minks and blue fox;

(3) infectious activity in the Japanese quail embryo cell culture;

(4) antigenic activity;

(5) immunogenic activity (in the neutralization test on the Japanese quail embryo cell culture);

(6) absence of contaminating viruses;

(7) bacterial sterility and the absence of PPLO mycoplasms;

(8) stability in storage;

(9) absence of contagiosity.

The seed virus is prepared from said strain, characterized by the above listed properties, on the Japanese quail embryo cell culture. The seed virus should be characterized by the same properties as specified for the strain of the virus. The seed virus is kept in the frozen state at a temperature not above minus 20° C. and used in the required quantities.

A trypsinized cell culture of Japanese quail embryos is used for the manufacture of the vaccine. The culture is prepared from 9–10 day old quail embryos which are crushed and trypsinized by the known method. The obtained cell suspension is inoculated with the seed virus and a suitable nutrient medium is added. Known media that are usually used to cultivate cells and viruses, e.g. medium 199, containing 10 percent of cattle serum (pH 7.0–7.5), are used as the culture medium. The inoculated medium is incubated in rollers at a temperature of 35±1° C. As soon as a monolayer of cells is formed, and 20–40 percent of cells show cytopathic action, the first harvest of the fluid containing the virus is collected. In order to increase the harvest of the virus and to ensure more complete utilization of the cell culture, the harvesting of the virus-containing fluid from the same sample of the culture is repeated several times, fresh portions of the nutrient medium being added after each harvest. This operation is repeated until the cell culture is completely degenerated.

In order to recover the intracellular virus, the cell culture is frozen and then defrosted. The collected fluid containing the virus is tested for sterility and infectious activity, and collected in one vessel. A stabilizing agent is added, and the fluid is filled into ampoules or vials and lyophilized. The dried preparation contains 3 percent by weight of residual moisture.

The lyophilized preparation can be kept for at least one year. The lyophilized vaccine should be kept at a temperature not above 4° C. If stored at lower temperatures, this term can be prolonged by several months. A saline solution prepared on the basis of the Henks solution should be used to dilute the dry preparation for vaccination purposes.

The obtained vaccinal preparation is tested for sterility, harmlessness, specificity, the absence of contaminating viruses, infectious activity, immunogenic and antigenic activities, and residual moisture. After these tests the vaccine can be used for prophylactic immunization of fur-bearing animal and dogs, as well as for therapeutic purposes in the course of the first days following the contact of the animal with a distemper affected one. The mean dose to vaccinate an animal should be not less than 10 $TCD_{50}$ (median tissue cytopathic dose). A dose containing to 100,000 $TCD_{50}$ does not produce undesirable reaction in the animals.

The animals are immunized by intramuscular injections of 1.0 ml of the vaccine.

To make sure the vaccination has been effective, the immunized animals can be given a serological examination in 10–14 days after the vaccination, and the titres of the antibodies determined in the neutralization reaction on a cell culture of Japanese quail embryos, using said vaccinal strain, giving a marked cytopathic effect, as the antigen. Antibodies are revealed in all immunized animals in the titre of 1:16–32. The maximum accumulation of antibodies (in the titre of 1:256) is attained by the 30th day. The antibodies are revealed in the blood during 18 months following the vaccination. In subsequent challenge of the immunized animals with the virulent strain Snyder Hill in 1, 3, 6, 12 and 18 months after the immunization with the proposed vaccine, none of the animals developed the disease. The proposed vaccine can thus be considered to have 100 percent immunogenic and antigenic activity.

The proposed vaccine was used at a farm at the moment of the outbreak of distemper among silver fox. The vaccination stopped the disease within a month and no cases of distemper were reported at later periods. A mink farm was located by side of the silver fox farm, and due to high contagiosity of the distemper virus, single cases of plague among minks were reported. The vaccination of the minks, that followed immediately, prevented the outbreak of the disease at the farm.

The obtained data indicate the potency of the vaccine prepared from the strain EPM 10–76 of the virus of canine distemper to eradicate an outbreak of distemper in the course of three or four weeks.

The proposed vaccine can also be used to immunize animals by giving it in aerosol form.

The vaccine prepared for injection, i.e. usual commercial batches of the vaccine, can be used for aerosol. The aerosol can be used to immunize a large number of animals within a short period of time.

Tests of the proposed vaccine on animals during prophylaxis of distemper showed that practically 100 percent of immunized animals produce antibodies in high titres to reliably protect the animals from distemper. Moreover, the vaccine has proved effective as a means of eradicating the focus of the disease.

The proposed vaccine is comparatively cheap because the cell culture of Japanese quail embryos is used as the substrate. This culture has the following advantages over the other known cultures. The main advantage is that Japanese quails are naturally immune toward viruses of avian leukemia and are resistant toward this infection.

An other important advantage of the Japanese quail embryo cell culture is its high proliferative activity and the monolayer of the cells is formed by the first or second day following seeding the cells.

Still another advantage of said culture is that the cell suspension can be infected. This shortens even more the time of the process of manufacturing the vaccine. An advantage of the invention is also that the fluid containing the virus can be harvested several time from one inoculum (to five harvests from one culture sample).

Japanese quails are readily available and cheap, their raising at special farms is simple and does not require much investment. All this explains the high commercial value of the proposed vaccine.

To make the invention more understandable to those skilled in the art, the following examples are given by way of illustration, in which Example 1 shows how to obtain the EPM 10–76 virus of canine distemper, Example 2 illustrates the method of preparing the live culture vaccine, and Examples 3 through 9 illustrate the method of using the vaccine.

EXAMPLE 1

Preparation of Attenuated Strain EPM of the Virus of Canine Distemper, Deposited under the Code Number 10–76, Isolated from the Wild Virulent Virus Into 10 test tubes, containing the primary cell culture of dog kidneys, added are 0.2 ml of defibrinized blood of a mink with distemper. After a three-hour contact at room temperature, the cell culture is washed thoroughly with a nutrient medium 199, 1.5 ml of fresh nutrient medium 199 containing 10 percent of cattle blood serum are added, and the cell culture is incubated at a temperature of 37° C. The nutrient medium is renewed once or twice a week. The fluid containing the virus is collected in the course of 62 days following the inoculation. The culture fluid is used to inoculate a new portion of the dog kidney cell culture. To that end, 0.3 ml of the fluid containing the virus and 1 ml of the nutrient medium 199 containing 10 percent of cattle blood serum are added to each of the ten test tubes containing new portions of the primary cell culture of dog kidneys. The cell culture is cultivated at a temperature of 37° C.

The fluid containing the virus, which is collected 35–40 days following the infection of the previous cultures, is used as the inoculum for the first ten passages. In the next 23 passages of the virus, the fluid containing the virus, which is collected 15–20 days following the infection, and also the virus isolated from the infected cells after the frosting-defrosting cycle, are used as the inoculum.

Next, after infection by a similar method, the virus is given 12 passages in the continuous cell culture of the human embryo Rh at 32° C. The fluid containing the virus, collected the 15–20th day following the previous infection, is used as the inoculum for each next infection.

The virus is further attenuated by passage on a mixed culture consisting of 2 million cells of dog kidneys and 2 million cells of Japanese quail embryo. The process is carried out a temperature of 35° C. The virus is given three passages on this culture. Then, the virus is passed five times on a cell culture of Japanese quail embryo at a temperature of 35° C. in rollers at 4 rpm. Beginning with the fifth passage, the virus regularly produced cytopathic destruction of cells, which was obvious 5–7 days following the infection. This virus was cloned by the limit dilution method in the cell culture of Japanese quail embryos and used as the vaccinal strain. The obtained attenuated strain of the virus of canine distemper adapted to the cell culture of Japanese quail embryos, is tested for the following:

(1) specificity in reactions of neutralization on the Japanese quail embryo cell culture (identification test);
(2) harmlessness (on laboratory animals, e.g. mice, guinea pigs, rabbits, minks, blue fox, and also embryos);
(3) infectious activity in the Japanese quail embryo cell culture;
(4) antigenic activity;
(5) absence of contaminating viruses;
(6) immunogenic activity;
(7) bacterial sterility, absence of mycoplasms (PP10);
(8) stability in storage;
(9) absence of contagiosity.

EXAMPLE 2

Preparation of Seed Virus and Vaccine:

(a) Preparation of Seed Virus. The seed virus is prepared from the strain EPM 10–76 obtained as described in Example 1. To this end, 9–11 day old embryos of Japanese quails obtained from a special farm are used. Hundred embryos are trypsinized by the known method to obtain 3,300,000,000 cells that are suspended in 4.120 liters of nutrient medium 199 containing also 10 percent of cattle blood serum and 100 mg/ml of monomycin. 150-ml portions of the cell suspension are placed into two one-liter flasks and kept as control. 10 ml of a culture fluid containing the strain EPM 10–76 are added to the remaining portion of the cell suspension and 150-ml portions of the suspension are placed into one liter flasks. The suspension in the flasks is incubated at a temperature of 35° C. in rollers. Three days following the inoculation, the nutrient medium is removed and fresh portions of the medium are added into all flasks. The medium 199 should contain 100 mg/ml of monomycin. On the sixth day following the inoculation, if the fluid containing the virus shows the cytopathic activity, the fluid is withdrawn from the flasks, its samples are taken for the corresponding tests, and fresh portions of medium 199 are added. Next harvesting of the virus-containing fluid is continued until 50 percent of cells are retained. Now 70 ml of fresh medium 199 are added, the cell culture is frozen in dry ice, and then defrosted to isolate the intracellular virus.

Samples are taken at each stage of preparing the seeding virus, which should pass the following tests: for specificity (identity), harmlessness, infectious activity, antigenic activity, immunogenecity, absence of contaminating viruses, sterility, and the absence of contagiosity. The seeding virus meeting said requirements is kept frozen at a temperature not above minus 20° C.

(b) Preparing the Vaccine. 9–11 day old embryos of Japanese quails obtained from a special controlled farm are used for the purpose. 200 embryos are trypsinized by the known method to obtain 6,600,000,000 cells that are suspended in 8.250 liter of nutrient medium 199. 10 percent of cattle blood serum and 100 mg/ml of monomycin are added to the medium. 150-ml portions of the cell suspension are placed into five one-liter flasks (750 ml all altogether) and kept for control purposes. 10 ml of culture fluid containing the seeding virus of strain EPM 10–76, obtained in item (a) are added to the remaining cell suspension, and its 150-ml portions are placed into one-liter flasks. All the flasks are now cultivated at 35° C. in rollers. On the third day after seeding, the nutrient medium is removed and fresh medium 199, containing 100 mg/ml of monomycin, is added instead. On the sixth day following the inoculation, as the foci of cytopathic activity appear in 30 percent of the cells, the virus-containing fluid is removed, its samples are taken for control purposes, and fresh medium 199 is added into all flasks. The harvesting is repeated until 50 percent of the cells are retained and 70 ml of medium 199 are finally added. The cell culture is now frozen and defrosted to isolate the intracell virus.

All sterile virus harvests are joined in one vessel, a stabilizing agent consisting of 5 percent of sorbitol and 1.5 percent of gelatose is added, the vaccine is filled into vials or ampoules, and lyophilized. The pool makes one batch of the vaccine. The obtained vaccine can be filled into vials or ampoules of various capacity, from 1 to 33 ml, and contain from 1 to 500 doses in one ampoule or vial, depending on the consumer demand.

Control samples of the vaccine are taken at each stage of the process. The vaccine should be tested for the following: identity, harmlessness, infectious activity, antigenic and immunogenic activity, the absence of contaminating viruses, sterility, and the absence of contagiosity.

A batch of the vaccine meeting these requirements can be used to immunize animals. In our example, a batch of the vaccine contains 360,000 doses.

EXAMPLE 3

Testing for Harmlessness

The vaccine was used in a dose of 1 ml containing 100 $TCD_{50}$ of the virus diluted with Henks solution. The vaccine was injected intramuscularly. 24 mink cubs and 12 blue fox cubs were immunized. 16 cubs of mink and 8 of blue fox were kept as controls. The vaccinated animals were observed daily for 28 days. All the animals remained clinically healthy. Pathological reactions, such as refusal of food, suppression, alimentary disorders, were not observed. The animals that were kept in contact with the vaccinated animals did not develop the disease.

EXAMPLE 4

Testing for Antigenic Activity

The animals were vaccinated with the preparation in doses as specified in Example 3, and blood samples were taken from them in 10-14 days following the vaccination. The titres of antibodies in the neutralization test on the cell culture of Japanese quail embryos were determined. The vaccinal strain EPM 10-76 of the virus of canine distemper was used as the antigen. The antibodies were determined in all animals in the titre of 1:16-32. The maximum accumulation of antibodies (in the titre of 1:256) was attained by the 30th day. The antibodies were found in the course of 18 months of observation.

EXAMPLE 5

Testing for Immunogenic Activity and Duration of Immunity (a) 24 cubs of mink and 12 of blue fox were given intramuscularly 1 ml of the dilute vaccine containing 100 $TCD_{50}$ of the virus. 16 cubs of mink and 8 of blue fox were kept for control purposes. The vaccinated animals were challenged and the controls were then infected with a virulent virus (Synder Hill for the minks and Gauiasski for blue fox) on the 30th day following the immunization. The animals were observed daily. The controls (not immunized animals) perished from distemper, whereas the vaccinated animals did not respond to the administration of the virulent strain. During the entire time of observation (21 days following the infection) the vaccinated animals remained healthy clinically.

(b) In 18 months after the vaccination, the animals were challenged again with the virulent viruses Snyder and Gauiasski. None of the repeatedly infected animals perished or developed distemper.

EXAMPLE 6

Testing the Vaccine in Field Conditions

In the course of the summer vaccination for prophylactic purposes, 1,400,000 foxes, 45,500 blue foxes, 300,000 minks and 255,000 dogs were vaccinated. All vaccinated animals did not develop distemper although outbreaks of the disease were reported in the surrounding regions.

EXAMPLE 7

Testing the Vaccine in the Focus of Canine Distemper

The vaccine was tested at a farm where multiple cases of plague of carnivores were revealed among young silver fox (proved by laboratory analysis). The mortality rate was 120 cubs a day. All animals at the farm were then vaccinated. The mortality rate decreased two times in two months, and by the end of the third month the animals stopped perishing.

Single cases of distemper were reported from a mink farm located near the silver-fox farm. All animals were vaccinated and the outbreak of plague was thus prevented.

EXAMPLE 8

Comparison of the Proposed and the known Preparations

All animals were immunized with the known vaccine KF-668 (USSR) at a mink farm with multiple cases of canine distemper among cubs. After the vaccination the mortality rate did not diminish and was 180 cubs a day. 14,612 animals were immunized repeatedly with the proposed vaccine and 15,580 animals with the known, ASL vaccine (USA). Following the repeated immunization with said vaccines the mortality among the cubs decreased markedly, and in two months the outbreak of distemper was eradicated completely. Thus the proposed vaccine proved to be no less efficaceous than the known vaccine ASL.

EXAMPLE 9

Testing the Vaccine in Aerosol Form

The vaccine was prepared by the process as described above (for intramuscular injections). It was used in aerosol form to immunize 300 cubs of mink, aged 45-60 days. One group of the animals was exposed to the sprayed aerosol so that each animal was given one dose of the vaccine whereas in the other group the animals were given to inhale three doses. By one dose we understand here a usual dose for intramuscular injection. The antibodies to the distemper virus were determined in the blood serum of the immunized animals by the neutralization reaction on the Japanese quail embryo cell culture, using the vaccinal strain EPM 10-76 as the antigen. The antibodies were determined in the dilution of 1:8 for the minks vaccinated with one dose and in the dilution of 1:32 for the animals vaccinated with three doses.

We did not observe significant difference in the titres of the virus-neutralizing antibodies in the animals vaccinated intramuscularly (as described in Example 4) and those vaccinated with the preparation in aerosol form.

The duration of immunity in the animals vaccinated with the preparation in aerosol form was tested by challenging the animals with the virulent virus Synder Hill. The animals vaccinated with the proposed vaccine did not develop distemper after the infection with the virulent strain of the virus.

Example 9 shows that the proposed vaccine obtained from the strain EPM 10-76 of the virus of canine distemper intended for intramuscular injections is as efficaceous for vaccination of the animals with the preparation in aerosol form.

What is claimed is:

1. A living virus culture vaccine against canine distemper comprising an attenuated strain EPM 10-76 of the virus of canine distemper, said strain being obtained by first isolating the wild virus from the blood of a mink with distemper, and then conducting a series of multiple passages of the wild virus on the following cultures in seriatim: (1) a dog kidney cell culture, (2) a continuous cell culture of the kidneys of human embryo Rh, and (3) a mixed culture consisting of dog kidney cells and Japanese quail embryo cells; adapting the resulting attenuated strain by conducting multiple passages on a Japanese quail embryo cell culture; and cultivating the resultant strain on a Japanese quail embryo cell culture in a suitable culture medium.

2. A method of preparing a living virus culture vaccine against canine distemper comprising an attenuated strain EPM 10-76, the method comprising the steps of isolating a wild canine distemper virus from the blood of a mink with distemper; conducting a series of multiple passages of the virus on the following cell cultures in seriatim: (1) a dog kidney cell culture, (2) a continuous cell culture of the kidneys of the human embryo Rh, and (3) a mixed culture consisting of dog kidney cells and Japanese quail embryo cells; adapting the resulting attenuated strain by conducting multiple passages on a Japanese quail embryo cell culture; cultivating the resulting strain on a Japanese quail embryo cell culture in a suitable culture medium; collecting the virus-containing fluid; and lyophilizing the collected virus-containing fluid in the presence of a suitable stabilizing agent.

3. The method of claim 2, wherein the multiple passage sequence comprises conducting in seriatim from 20 to 40 passages on the dog kidney cell culture at a temperature of from about 36°–38° C., from 5 to 15 passages on the cell culture of the kidneys of human embryo Rh at a temperature of from about 31°–33° C., and from 2 to 7 passages on the mixed culture consisting of dog kidney cells and Japanese quail embryo cells at a temperature of from about 34°–36° C.; and wherein the adaptation step is carried out by conducting 4 to 10 passages on the Japanese quail embryo cell culture.

4. The method of claim 2, wherein the collecting step is first conducted after the appearance of cytopathic action of the virus in from about 20 to 40 percent of the cells of the culture.

5. The method of claim 2, wherein the virus-containing fluid is lyophilized in the presence of from about 4.5 to 5.5 weight percent of sorbitol and from about 1.4 to 1.6 weight percent of gelatose.

* * * * *